(12) United States Patent
Yang et al.

(10) Patent No.: US 7,399,598 B2
(45) Date of Patent: Jul. 15, 2008

(54) DIAGNOSIS METHOD OF ENDOMETRIOSIS BY DETECTING BIOCHEMICAL MARKERS AND USAGE OF THESE BIOCHEMICAL MARKERS

(75) Inventors: Wei-Chung Yang, Taipei (TW);
Chii-Ruey Tzeng, Taipei (TW);
Hwei-Jiung Wang, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 11/250,536

(22) Filed: Oct. 14, 2005

(65) Prior Publication Data

US 2007/0087386 A1 Apr. 19, 2007

(51) Int. Cl.
*G01N 33/53* (2006.01)
(52) U.S. Cl. ............... 435/7.1; 435/7.92; 436/501; 436/518
(58) Field of Classification Search .......... 435/6, 435/7.1, 7.92–7.94; 436/501, 518, 811
See application file for complete search history.

(56) References Cited

U.S. PATENT DOCUMENTS

| | | | | |
|---|---|---|---|---|
| 5,063,152 | A * | 11/1991 | Nagasawa et al. | 435/24 |
| 2003/0124551 | A1* | 7/2003 | Pappa et al. | 435/6 |
| 2003/0157580 | A1* | 8/2003 | Hochstrasser et al. | 435/7.93 |
| 2005/0112560 | A1* | 5/2005 | He et al. | 435/5 |
| 2006/0063204 | A1* | 3/2006 | Valkirs et al. | 435/7.1 |

OTHER PUBLICATIONS

Drews et al., Acute Phase Proteins in Endometriosis, Annals of the New York Academy of Sciences, vol. 762, 1995, pp. 508-509.*
Boutten et al., IL6 and acute phase plasma proteins in peritoneal fluid of women with endometriosis, Clinica Chimica Acta, 210 (1992) 187-195.*
Bedaiwy et al., Laboratory testing for endometriosis, Clinica Chimica Acta 340 (2004) 41-56.*
Medicine Net.com, Adenomyosis definition—Medical Dictinary definitions of popular medical terms, pp. 1-3, 2007.*
Asgerally T. Fazleabas, Ph.D., Firyal S. Khan-Dawood, Ph.D., M. Yusoff Dawood, M.D.; Protein, progesterone, and protease inhibitors in uterine and peritoneal fluids of women with endometriosis; Fertility and Sterility, Feb. 1987; pp. 218-224; 47:2; Elsevier, Inc.; USA.
Definition of Endometriosis interna. [online]. 1 page. [retrieved on Dec. 13, 2007]. Retrieved from the Internet: < URL: http://www.medterms.com/script/main/art.asp?articlekey=7029&pf=3&page=1>.
Definition of Endometriosis uterina. [online]. 1 page. [retrieved on Dec. 13, 2007]. Retrieved from the Internet: < URL: http://www.medterms.com/script/main/art.asp?articlekey=7030&pf=3&page=1>.
Shiel et al., Endometriosis. [online]. 7 pages. [retrieved on Dec. 13, 2007]. Retrived from the Internet <: URL: http://www.medicinenet.com/script/main/art.asp?articlekey=356&pf=3&page=1>.

* cited by examiner

*Primary Examiner*—Long V. Le
*Assistant Examiner*—Gary W. Counts
(74) *Attorney, Agent, or Firm*—Schmeiser, Olsen & Watts

(57) ABSTRACT

The present invention relates to a non-invasive diagnosis method of endometriosis by detecting biochemical marker in serum or peritoneal fluid, in particular alpha 1-antitrypsin, fragments of alpha 1-antitrypsin, or a combination of both. The diagnosis of endometriosis is performed with observing in serum specimens of a patient the concentration and change of the biochemical marker, in particular molecules related to alpha 1-antitrypsin, and comparing with a predetermined baseline level of the biochemical marker contained in serum. Statistical analysis can be performed to evaluate the baseline level indicating the occurrence of endometriosis. Therefore, the present invention can provide an auxiliary guideline for the diagnosis of endometriosis. The present invention also relates to usage of the biochemical marker.

8 Claims, 13 Drawing Sheets

DIAGNOSIS METHOD OF ENDOMETRIOSIS BY DETECTING BIOCHEMICAL MARKERS AND USAGE OF THESE BIOCHEMICAL MARKERS

BACKGROUND OF THE INVENTION

1. Field of the Invention

The present invention relates to a new diagnosis method of endometriosis by detecting biochemical marker in serum, in particular alpha 1-antitrypsin, fragments of alpha 1-antitrypsin, or a combination of both.

2. Description of the prior art

Endometriosis has been a disease which is most frequently found in women at reproductive age [Guarnaccia et al. 1997]. Many pre-menopausal women suffer from endometriosis over a long period of time. The most common symptom is menstrual pain whereas in serious cases endometriosis may cause woman's infertility [Giudice et al., 2004]. Researchers have been making efforts in realizing the aetiology of endometriosis. Although its treatment have become easier, the mechanism leading to endometriosis is not clear so far. With respect to women without any disease symptoms the prevailing rate of endometriosis is 2%-22%. With respect to women with disease symptoms (e.g. menstrual difficulties, menstrual pain) the prevailing rate of endometriosis is.40%-60% [Farquhar, 2000; Kyama et al., 2003]. Among the women who suffer from menstrual pain during their menstrual period there are 13%-33% that suffer from infertility [D'Hooghe, et al., 2003]. Endometriosis is a disease characterized by the presence of endometrial tissue at ectopic sites, i.e. glands and stroma cells of endometrium which should grow inside the uterus grow at sites outside the uterus, preserving the same physiological form of a normal endometrium. Human uterine wall consists of three layers: endometrium, myometrium, and porous layer (from inside toward outside). Endometrial cells at ectopic sites also exhibit periodic changes due to influence of hormones, e.g. proliferation, degradation, bleeding, etc. If the nidus occurs at myometrium, it is called as adenomyosis. If the nidus occurs in the ovary, it is called chocolate cyst. If the nidus occurs at the pelvic cavity, it is called as pelvic endometriosis [Sampson et al., 1921].

In the diagnosis endometriosis is usually discovered based on the pain during patient's menstrual period and physiological inspections of abdominal cavity. Serious pain may be accompanied by pain of the rectum, even resulting in fever. However, if only symptoms are considered, the discovery may be delayed, leading to more serious condition. Therefore, the diagnosis of endometriosis has to be based on a combination of a variety of many observations and scientific inspection methods, including filtering symptoms, analyzing disease history, inferring according to clinical information. With help of palpation and methods such as ultrasonic diagnosis conjecture can be made about condition of the abdominal cavity and the pelvic cavity. Nevertheless, the gold standard of the diagnosis still depends on laparoscopy, in order to confirm the occurrence of endometriosis.

Although laparoscopy provides the gold standard of endometriosis, its acceptance is quite low because of the need of invasive procedure. Furthermore, laparoscopy in which endometriosis is to be observed optically has drawbacks such as difficulties in discovering the nidus at some sites, e.g. back sites of the pelvic cavity, sites surrounding intestines and stomach. On the other hand, vaginal ultrasonic method and nuclear resonance imaging (MRI) are taken to observe endometriosis occurring at the abdominal cavity and the ovary. These two techniques are more sensitive with respect to fibroid or chocolatecyst of more than 2 centimeter, but their sensitivity with respect to endometriosis is still very low. Barbieri in 1986 first proposed that CA125 in serum of a patient with endometriosis increases [Barbieri, 1986]. It is to be noted that an increase of CA125 usually relates to several physiological and pathological conditions, e.g. arrival of menstrual period, pregnancy, inflammation of the abdominal cavity, intimal arteritis, breast cancer, liver cancer, lung cancer, etc. The sensitivity is only about 15% to endometriosis. Because especially in the early stage of endometriosis CA125 shows almost no increase, the practical use of CA125 as a marker is limited. Only for cases in which CA125 has increased before the operation, it can be taken as a trail for reference. It is still to be noted that ovary tumor is found in patients of endometriosis as well as ovary cancer. CA125 increases in both cases that can not be differentiated in spite of performing specific Doppler-ultrasonic inspection on the blood stream. In general, CA125 in patients of endometriosis is usually about 100 U/ml and hundreds or even thousands times higher in patients of ovary cancer. During the operation of a patient of chocolate cyst whose CA125 is above 500 U/ml, laparascopical inspections should be performed carefully. Very careful inspection and cytological analysis of ascites can not be left out to find suspicious nidus indicating ovary cancer and endometriosis that should be further pathologically analyzed [Acien et al., 1989; Kennedy et al., 1990]. In fact, in the diagnosis application of CA125, the level of CA125 in a patient's serum is measured monthly when menstrual sign begins. This helps to diagnose depth endometriosis. When the baseline level of CA125 in serum is set to be 25 U/ml, the sensitivity and specificity with respect to endometriosis are respectively 67% and 90%. Therefore, CA125 is now taken by some doctors as a help of diagnosing endometriosis. For the moment, ultrasonic and blood inspection can be taken as a reference for diagnosis. The ultimate determination still depends on high invasive inspection methods such as laparoscopy. Be assisted with the image taken by an endoscope, a clinical doctor can inspect in detail within the abdominal cavity, the uterus, the oviduct, the ovary, and intrusion of uterus sacrum's ligament. During the inspection the doctor can use electric burning or perform excision to remedy. But there are many empirical differences in laparoscopic observations. For endometriosis there can be small nidus or large cyst which may be dark brown, black, or even white or yellow due to thick walls. When in serious situation of endometriosis a cyst is broken and chocolate-like liquid flows out, adhesive and grey scare tissues, black granular, even bubble-formed or tear-formed cyst as flame-like nidus can be seen everywhere in the abdominal cavity. Only a very experienced doctor can make a correct diagnosis and performs the remedy at the same time.

Proteomic approaches are now adopted by scientists to detect occurrence of diseases or biochemical markers for cancer. Proteomics as a research field on biochemical markers has developed better and better. As related to dealing with specimen, analysis with uni- or two-dimensional gel electrophoresis, analysis of images, and mass spectrometry analysis there have been lots of reported researches[Anderson, 2002; Adkin et al., 2002; Chan et al., 2004 Chen et al., 2005, Zhou et al., 2004; Zhou et al., 2005].

In human serum alpha 1-antitrypsin is one of the proteins contained significantly in the serum. Its molecular weight is about 52 kDa. Alpha 1-antitrypsin is called as protease inhibitor (Pi) due to its action mechanism, belonging to the supergene family. Its main function is to reduce neutrophil elastase that is secreted by leukocytes in the immune system. Neutrophil elastase is a protease which assists human immune system in protecting from bacteria and foreign harmful materials. As to the structure alpha 1-antitrypsin exhibits three isoforms of differences in glycosylation, as characterized by three different structures formed with different amounts of oligosaccharide group and sialic acid [Carrell, 1982].

REFERENCE

Acien P, Shaw R W, Irvine L, Burford G, Gardner R. (1989)CA 125 levels in endometriosis patients before, during and after treatment with danazol or LHRH agonists. *Eur. J. Obstet. Gynecol. Reprod. Biol.* 32:241-246

Adkins J N, Varnum S M, Auberry K J, Moore R J, Angell N H, Smith R D, Springer D L, Pounds J G. (2002)Toward a human blood serum proteome: Analysis by multisimensional separation coupled with weight spectrometry. *Mol. Cell. Proteomics* 1:947-955

Anderson N L, and and Anderson N G. (2002)The human plasma proteome: History, character, and diagnostic prospects. *Mol. Cell. Proteomics* 1:845-867

Barbieri R L. (1986)CA125 in patients with endometriosis. *Fertil. Steril.* 45:767-769

Carrell R W, Jeppsson J O, Laurell C B, Brennan S O, Owen M C, Vaughan L, Boswell D R. (1982) Structure and variation of human alpha 1-antitrypsin. *Nature.* 298:329-334.

Chan K C, Lucas D A, Hise D, Schaefer C F, Xiao Z, Janini G M, Buetow K H, Issaq H J, Veenstra T D, Conrads T P. (2004) Analysis of the human serum proteome. *Clin, Prot.* 1:101-226

Chen Y Y, Lin S Y, Yeh Y Y, Hsiao H H, Wu C Y, Chen S T, Wang A H. (2005) A modified protein precipitation procedure for efficient removal of albumin from serum. *Electrophoresis.* 26:2117-27

D'Hooghe T M, Debrock S, Hill J A, Meuleman C. (2003) Endometriosis and subfertility: is the relationship resolved? *Semin. Reprod. Med.* 21:243-254.

Farquhar C M. (2000)Extracts from the "clinical exidence" Endometriosis. *BMJ.* 320:1449-1452

Giudice L C, Kao L C. (2004) Endometriosis. *Lancet.* 364:1789-1799

Guarnaccia M, Olive D L. (1997) The structure and future of endometriosis research. Obstet. *Gynecol. Clin. North Am.* 24:455-465

Kennedy S H, Mojiminiyi O A, Soper N D, Shepstone B J, Barlow D H. (1990) Immunoscintigraphy of endometriosis. *Br. J. Obstet. Gynaecol* 97:667-670

Kyama C M, Debrock S, Mwenda J M, Hooghe T M. (2003) Potential involvement of the immune system in the development of endometriosis. *Reprod. Biol. Endocrinol.* 1:123-131

Sampson J A. (1921)Perforating hemorrhagic (chocolate) cysts of the ovary, there importance and especially their relation to pelvic adenomas of endometrial type. *Arch. Surg.* 3:245-323.

Zhou M, Conrads T P, Veenstra T D. (2005) Proteomics approaches to biomarker detection. *Brief Funct. Genomic. Proteomic.* 4:69-75.

Zhou M, Lucas D A, Chan K C, Issaq H J, Petricoin E F 3rd, Liotta L A, Veenstra T D, Conrads T P. (2004) An investigation into the human serum "interactome". *Electrophoresis.* 25:1289-1298.

SUMMARY OF THE INVENTION

As described above, it is understood that the present medical technology can not provide low invasive and correct diagnosis of endometriosis. On the other hand, the well developed proteomic technique, as being an objective and effective method, can fast and simultaneously detect expressions and quantities of different proteins in a specimen. The main purpose of the present invention is to provide a diagnosis method of endometriosis, as to decrease patient's risks and lower medical cost.

The essential spirit of the present invention is detecting protein molecules as a biochemical marker which is highly related to endometriosis, wherein methods based on proteomic approaches are used. According to the present invention, the diagnosis of endometriosis is performed with observing in serum specimens of a patient the concentration and change of the biochemical marker, in particular molecules related to alpha 1-antitrypsin, and comparing with a predetermined baseline level of the biochemical marker contained in serum. Statistical analysis is performed to evaluate the baseline level indicating the occurrence of endometriosis. Therefore, the present invention can provide an auxiliary guideline for the diagnosis of endometriosis.

The method of the present invention as described above comprises the steps of: (i) detecting in a first serum specimen a biochemical marker, wherein said biochemical marker comprises alpha 1-antitrypsin, fragments of alpha 1-antitrypsin, or a combination of both; and (ii) comparing the level of said biochemical marker in the first serum specimen with a baseline level determined through measuring levels of said biochemical marker in serum specimens with endometriosis, wherein level of said biochemical marker greater in the first serum specimen as compared to the baseline level indicates endometriosis.

The present invention also provides a method of utilizing a biochemical marker comprising alpha 1-antitrypsin, fragments of alpha 1-antitrypsin, or a combination of both for endometriosis diagnosis by providing said biochemical marker with a diagnosis device.

In order that the nature of the present invention may be more clearly understood preferred forms thereof will now be described with reference to the following Examples, Figures and Tables.

DETAILED DESCRIPTION OF THE INVENTION

EXAMPLE 1

Identifying Proteins Contained in Serum

In the diagnosis method of the present invention proteins as the biochemical marker contained in serum can be detected and identified through separating the target proteins from the rest content of the serum. This can be achieved by various separation techniques, e.g. uni- or two-dimensional gel electrophoresis followed by appropriate identification analyses such as mass spectrometry. In electrophoresis different molecules are separated according to their masses and electric charges.

In the following an example is explained with the analysis results of two-dimensional gel electrophoresis.

Figure 1:
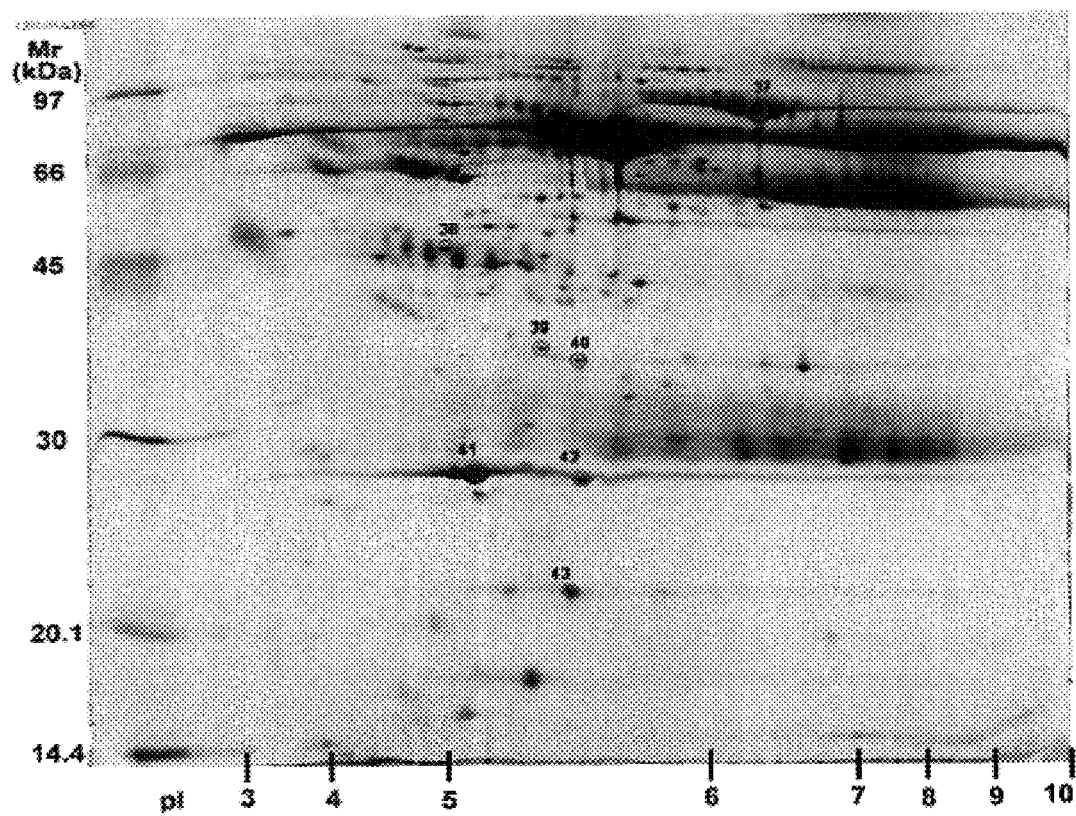
FIG. 1 and FIG. 2 show the image resulting from the two-dimensional gel electrophoresis.
Figure 2:
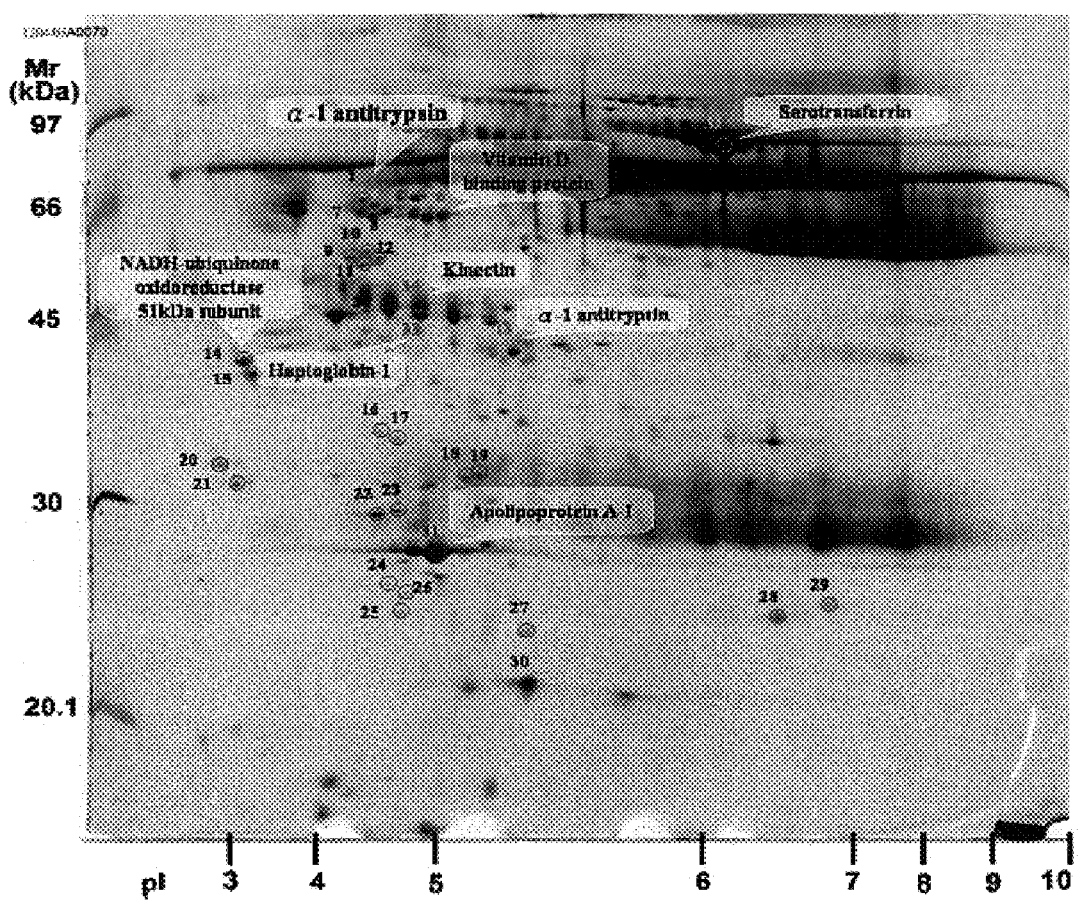

FIG. 1 and FIG. 2 show the representative images resulting from the two-dimensional gel electrophoresis performed for serum taken from the control group and an endometriosis patient respectively. For both the control group (FIG. 1) and the endometriosis case (FIG. 2) the serum specimen was at first treated by precipitation with 10% TCA/acetone. The protein loading was 300 μg. Isoelectric focusing electrophoresis (IEF) was performed with 18 cm pI3-10 non-linear immobilized strip, 18.5 cm×18.5 cm 12.5% SDS-PAGE, and SYPRO® Ruby protein staining, followed by 610 nm fluorescence image scanning with Typhoon™ 9200 Amersham Phamacia. The images shown in FIG. 1 and FIG. 2 are compared using the application program ImageMaster™ Amersham Phamacia. Red circles in FIG. 1 and FIG. 2 indicate proteins of different isoelectric focusing (X-axis) and different molecular weight (Y-axis) according to the comparison between the both images. As indicated with standard molecular weight in FIG. 2, seven proteins are identified with mass spectrometry. As shown in the results described above proteins that can be used as the biochemical marker for the diagnosis of endometriosis can be identified.

According to the diagnosis method of endometriosis of the present invention, the biochemical marker comprises alpha 1-antitrypsin, fragments of alpha 1-antitrypsin, or a combination of both.

In a preferred form of the present invention described above, the biochemical marker can be the whole molecule of alpha 1-antitrypsin or fragments thereof with an approximate molecular weight of 36 kDa, 45 kDa, or 52 kDa

EXAMPLE 2

Expressions of Alpha 1-antitrypsin in Relation to Endometriosis

According to the diagnosis method of the present invention proteins as the biochemical marker contained in serum is quantitatively analyzed and the level of the biochemical marker in serum is to be determined. The method for measuring the level of the biochemical marker is not restricted. The following example shows the measurement results of using the method of immuno-dot blot to measure the concentration of alpha 1-antitrypsin as the biochemical marker for determining the level of the biochemical marker in serum.

Figure 3A:
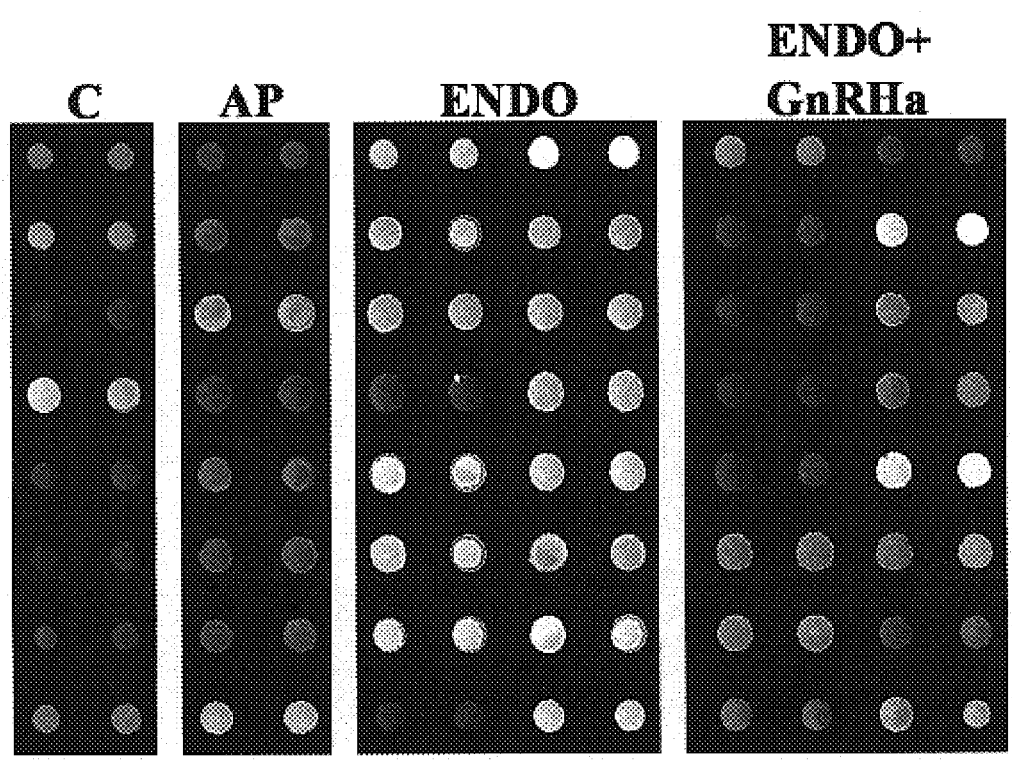
FIG. 3A shows an example of the experiment results with Immuno-dot blot.
Figure 3B:
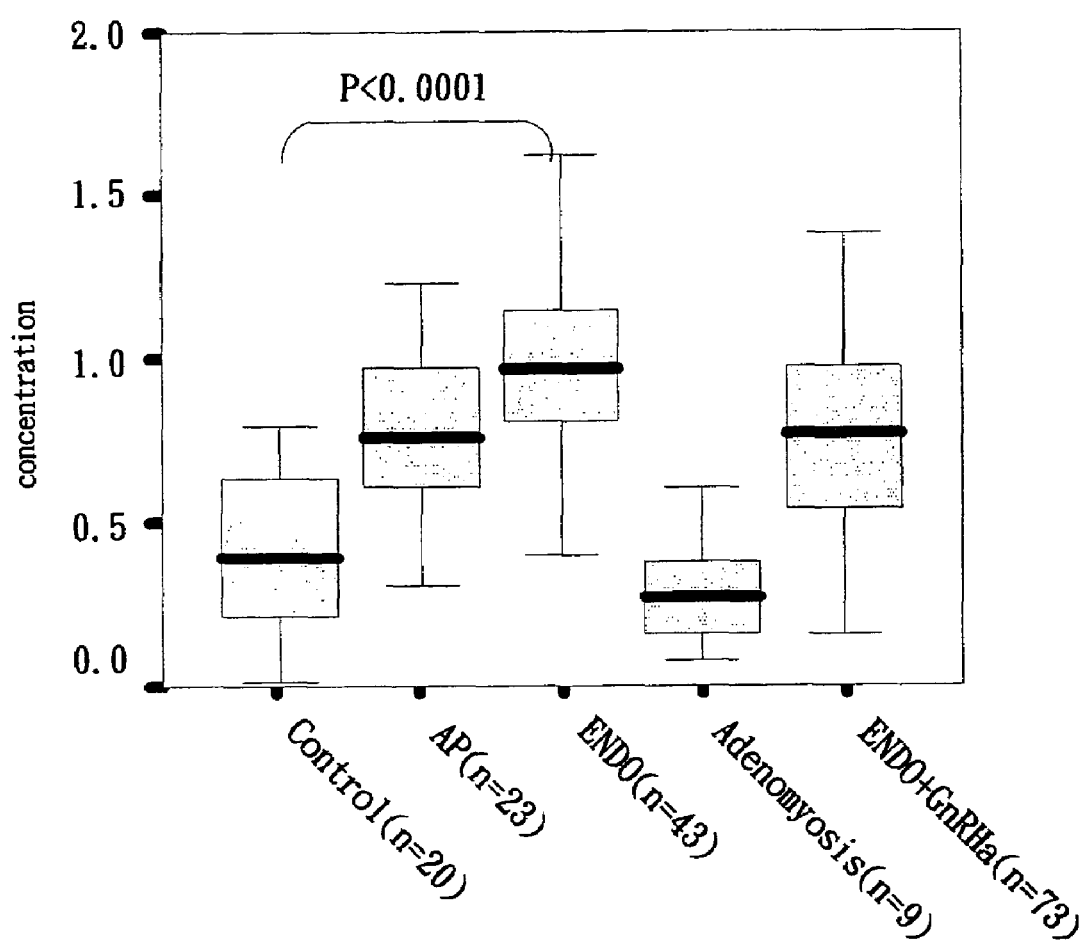
FIG. 3B shows the measured average concentration of alpha 1-antitrypsin in serum of healthy women at reproductive age as controls (n=20), pregnant women (AP, n=23), patients with pelvic endometriosis (ENDO, n=43), endometriosis patients diagnosed with adenomyosis (Adenomyosis, n=9), and patients with endometriosis following gonadotropin-releasing hormone analog treatment (ENDO+GnRHa, n=73).

FIG. 3A shows an example of the experiment results with Immuno-dot blot for quantifying the expression of alpha 1-antitrypsin contained in serum. Tested serum specimens were taken from subjects that are classified into four groups: 8 healthy women at reproductive age (Control), 8 women with pregnancy (AP), 16 women with endometriosis untreated (ENDO), 16 women with endometriosis treated with gonadotropin-releasing hormone analog, GnRHa (ENDO+GnRHa). It is seen that the expression of alpha 1-antitrypsin in the ENDO group is significantly higher than in the control group. FIG. 3B shows the average concentration of 1-antitrypsin measured for subjects that are classified into five groups: 20 healthy women at reproductive age (Control), 23 women with pregnancy (AP), 43 women with endometriosis untreated (ENDO), 9 women with Adenomyosis (Adenomyosis), 73 women with endometriosis treated with GnRHa (ENDO+GnRHa).

In a preferred form of the present invention described above, a statistical analysis is performed on the measured levels, so as to determine the difference between the measured levels. The method of the statistical analysis is not restricted. This is illustrated as follows with the present example. The results of the five groups were compared based on a statistical analysis of covariance (one-way ANOVA). It is found that the concentration of 1-antitrypsin in the AP group, ENDO group, and ENDO+GnRHa group shows a tendency of increase as compared with the control group. But only the ENDO group shows significance in the increase tendency ($p<0.001$).

In Table 1 the average concentrations of 1-antitrypsin are shown with mean±SEM and compared between the groups. The method of one-way ANOVA is taken to analyze the difference between groups, and Schiff's test is performed to evaluate the p-value between every two groups. A p-value with $p<0.05$ show that the difference between groups is significant. As shown in the results, the ENDO group is significantly different from the Control group with $p<0.0001$.

In Table 2 the results by applying the method of immuno-dot blot on 9 patients are shown. These results show changes of the concentration of alpha 1-antitrypsin contained in the serum before taking GnRHa as compared with that after taking GnRHa.

Figure 4:
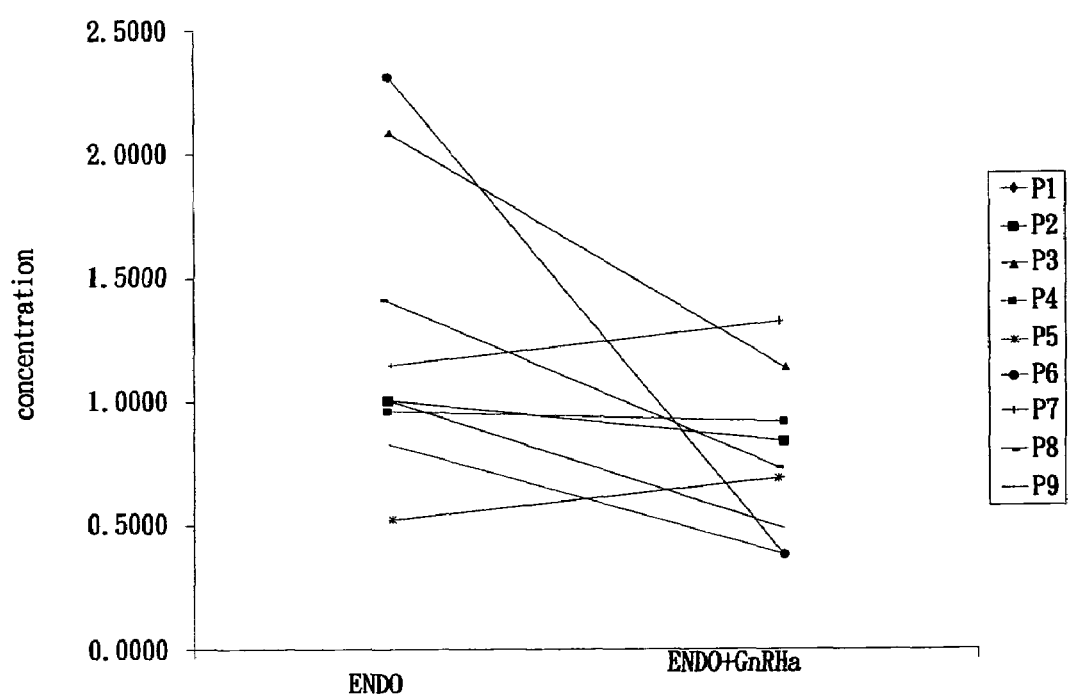
FIG. 4 shows the above result of the immuno-dot blot performed on a monitoring 9 individual patients with endometriosis before (ENDO) and after GnRHa treatment (ENDO+GnRHa).

FIG. 4 shows the above result of the immuno-dot blot performed on a single patient. A change of the concentration of alpha 1-antitrypsin after being treating with GnRHa is seen. It has been found that out of the all 9 patients there are 6 patients whose concentration of alpha 1-antitrypsin in the serum shows a decrease tendency.

For illustrating the general validity of the diagnosis method provided in the present invention, expressions of alpha 1-antitrypsin with respect to age and weight are shown in the following examples.

EXAMPLE 3

Expressions of Alpha 1-antitrypsin With Respect to Age and Weight

Table 3 shows the result of performing one-way ANOVA. Schiff's test is taken to quantify the concentration difference of alpha 1-antitrypsin between groups classified according to age and BMI (body mass index). The measurement results are shown with mean±SEM. The p-value represents the difference between the groups. When $p<0.05$, the difference is taken as statistically significant. n gives the number of tested patients of a group. NS means that the difference is non-significant. U/ml means total content of alpha 1-antitrypsin in pg that is contained in 100 µg serum. As shown in Table 3, the age of most tested patients is within 31-40 years and the BMI of most tested patients is within the normal range of 18.5-23. For the patients of age and BMI within the mentioned range the concentration of alpha 1-antitrypsin in serum is higher in the ENDO group as compared with the Control group, showing a significant difference with p<0.001.

EXAMPLE 4

Figure 5A:
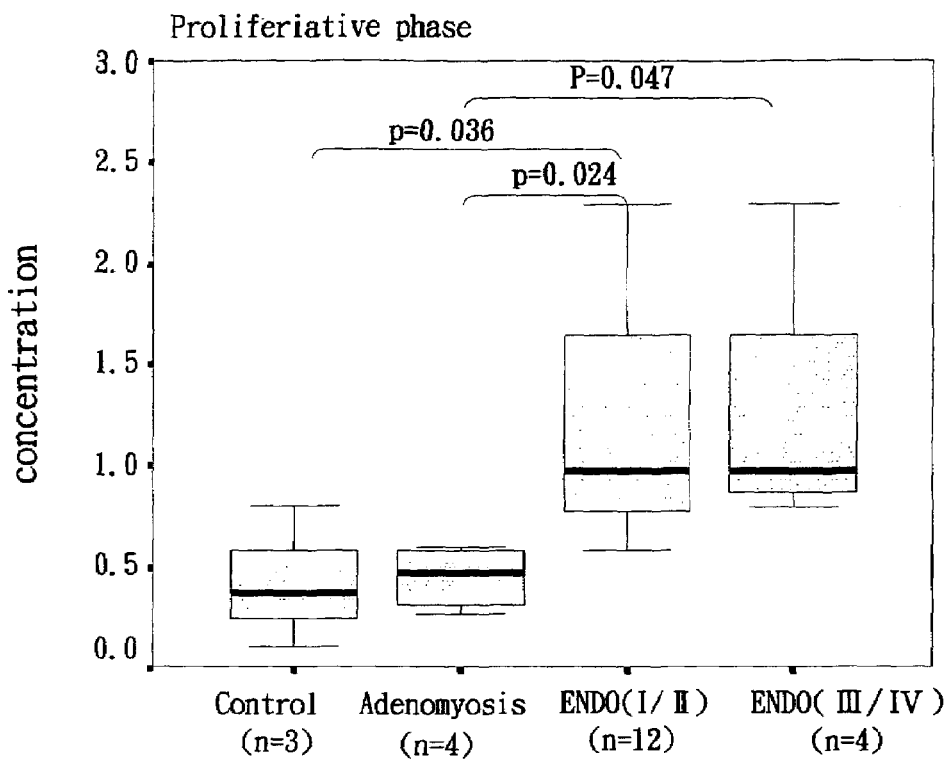
FIG. 5A and FIG. 5B show the measured concentration of alpha 1-antitrypsin in serum of the group in proliferative phase (P) and in secretory phase (S) respectively during menstrual cycle.
Figure 5B:
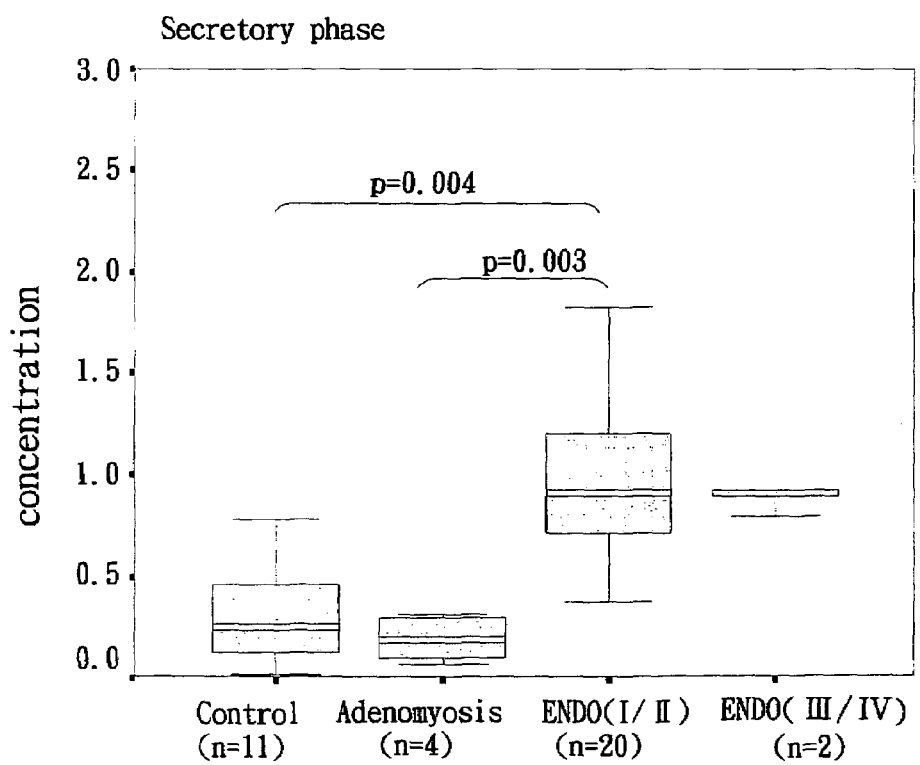

Expressions of Alpha 1-antitrypsin with Respect to Disease Stage and Woman Physiological Phase During Menstrual Cycle Expressions of alpha 1-antitrypsin with respect to disease stage and woman physiological phase are shown in the following example. Serum specimens of patients with endometriosis were classified into two groups: (1) the group of early disease stage corresponding to the stage I and II of endometriosis (ENDO(I/II)) and (2) the group of late disease stage corresponding to the stage III and IV of endometriosis (ENDO(III/IV)). All serum specimens were further classified into two groups according to patient's physiological period of (1) proliferative phase and (2) secretory phase. Concentration of alpha 1-antitrypsin in serum was measured for all groups. Differences between groups were analyzed. FIG. 5A and FIG. 5B show the results of the group in proliferative phase and in secretory phase respectively. Here, top and bottom edge of a box corresponds to the 75% and 25% quartiles. Thick middle line within the box represents the median. The top and bottom of the sign "I" shows the maximum and minimum values. Difference between groups is evaluated by performing one-way ANOVA with a post-test using the method of least significant difference (LSD). When the p-value conforms p<0.05, the difference is taken as significant.

Figure 6:
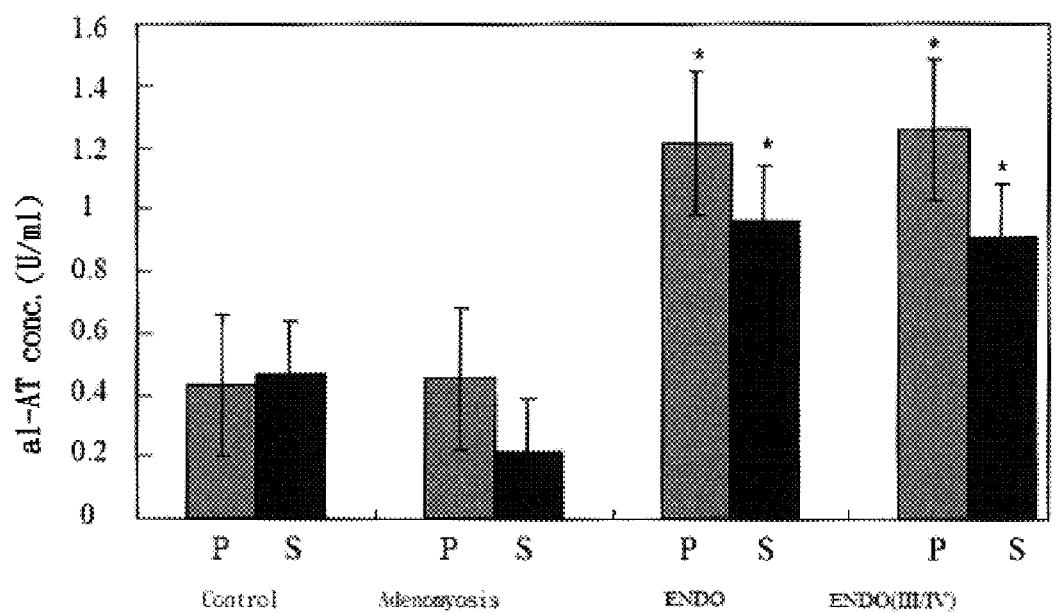
FIG. 6 shows the comparison with respect to the physiological period.

As shown in FIG. 6, the mean of measured results of all groups are compared with respect to the physiological period of the proliferative phase (P) and seretory phase (S). Here, the sign "I" represents standard derivation. The student's t test was performed to compare the concentration of alpha 1-antitrypsin measured on the group of proliferative phase with that measured on the group of secretory phase. When the p-value conforms p<0.05, the difference is taken as significant. It is seen that for patients with aAdenomyosis, early stages of endomatriosis (ENDO), and the late stages of endometriosis (ENDOIII/IV), the concentration of alpha 1-antitrypsin in the group of proliferative phase is higher than in the group of secretory phase. The concentration of alpha 1-antitrypsin in the group of early stages of endomatriosis (ENDO), and the late stages of endometriosis (ENDOIII/IV), the concentration of alpha 1-antitrypsin in both group of proliferative phase and secretory phase respectively is significantly higher than in the control group of both phases.

EXAMPLE 4

Determination of the Baseline Level of Alpha 1-antitrypsin

Figure 7:
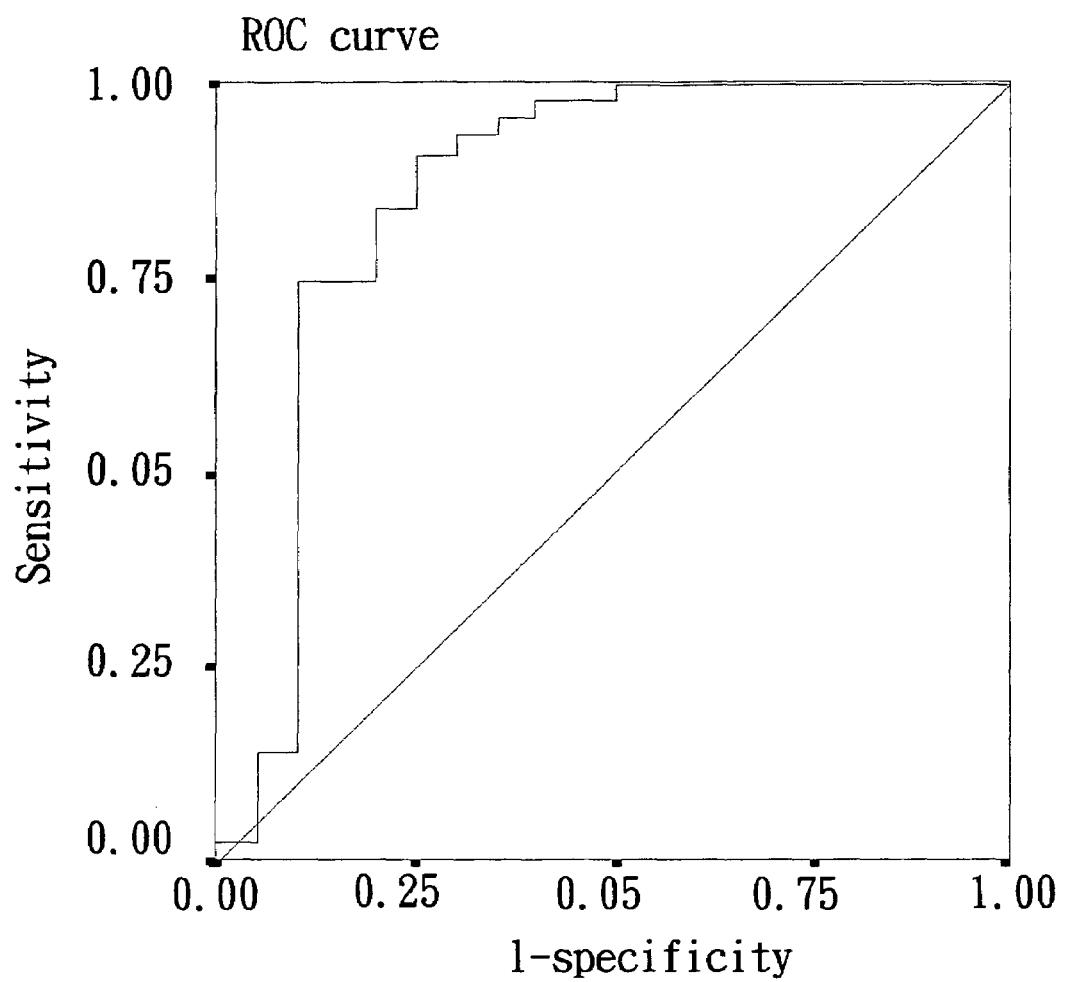
FIG. 7 shows the ROC curve with respect to the sensitivity and the value of 1-specificity.

The concentration of alpha 1-antitrypsin contained in serum specimens of the ENDO group is measured. Based on the measurement results the best baseline level of alpha 1-antitrypsin can be determined by analyzing a receiver operating characteristics curve (ROC). When the level of alpha 1-antitrypsin is greater in the serum of a subject as compared to the baseline level, endometriosis might be indicated. As shown in FIG. 7, a high sensitivity of 74.40% and a low 1-specificity of 10.00% can be obtained by taking a cut-off value of 0.812 U/ml as the baseline level of alpha 1-antitrypsin. This is summarized in Table 4.

In Table 5, sensitivity, specificity, positive predictive value (PPV) and Negative predictive value (NPV) are given in percentage. The biochemical marker is alpha 1-antitrypsin, CA125, any one of them or both of them, taking the cut-off value of 0.812 U/ml for alpha 1-antitrypsin and 35 U/ml for CA125. U/ml means total protein weight of alpha 1-antitrypsin in pg contained in 100 µg serum.

EXAMPLE 4

Effect of Protein Loading

Figure 8A:
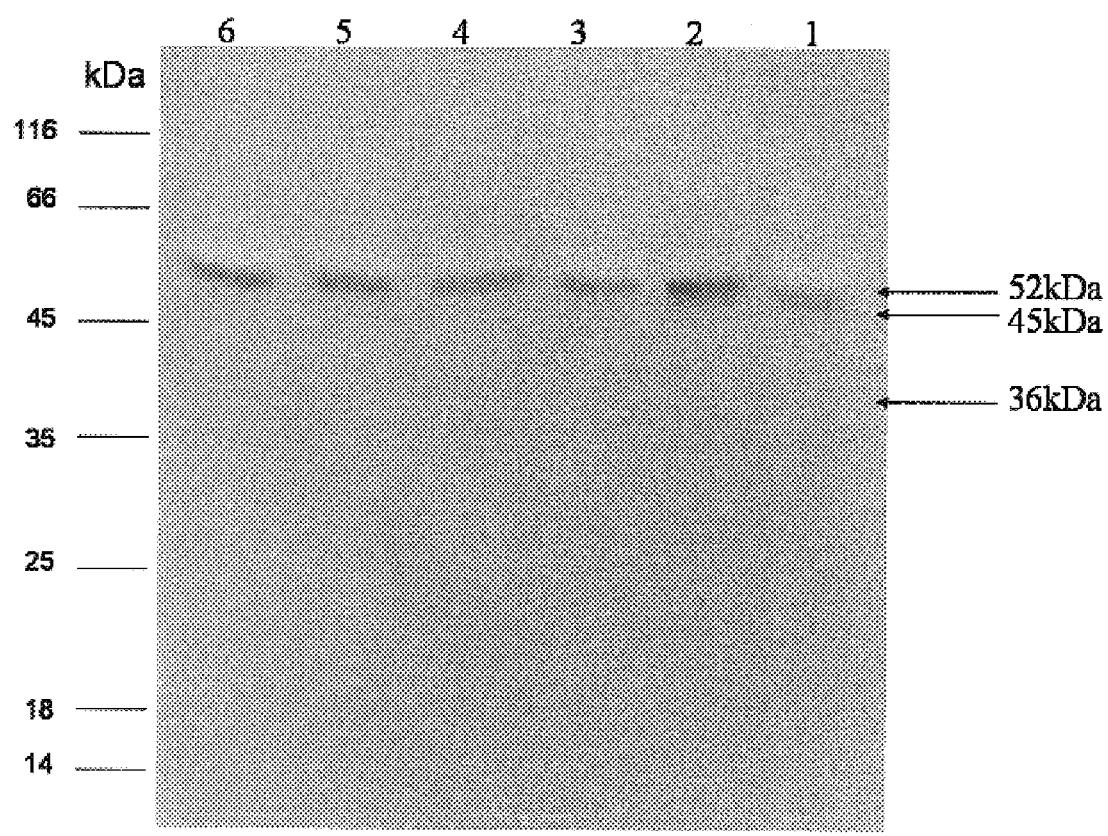
FIGS. 8A-8D show Western blotting observations of the effect of protein loading on expressions of alpha 1-antitrypsin in pooled serum specimens.
Figure 8B:
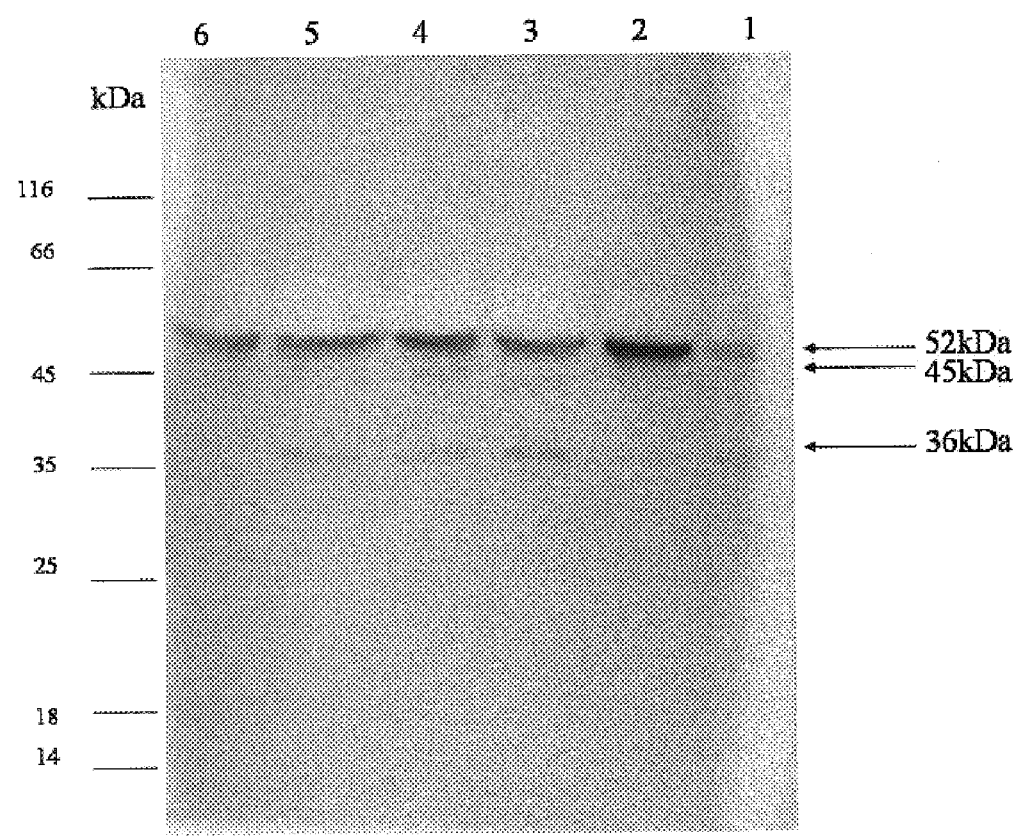
Figure 8C:
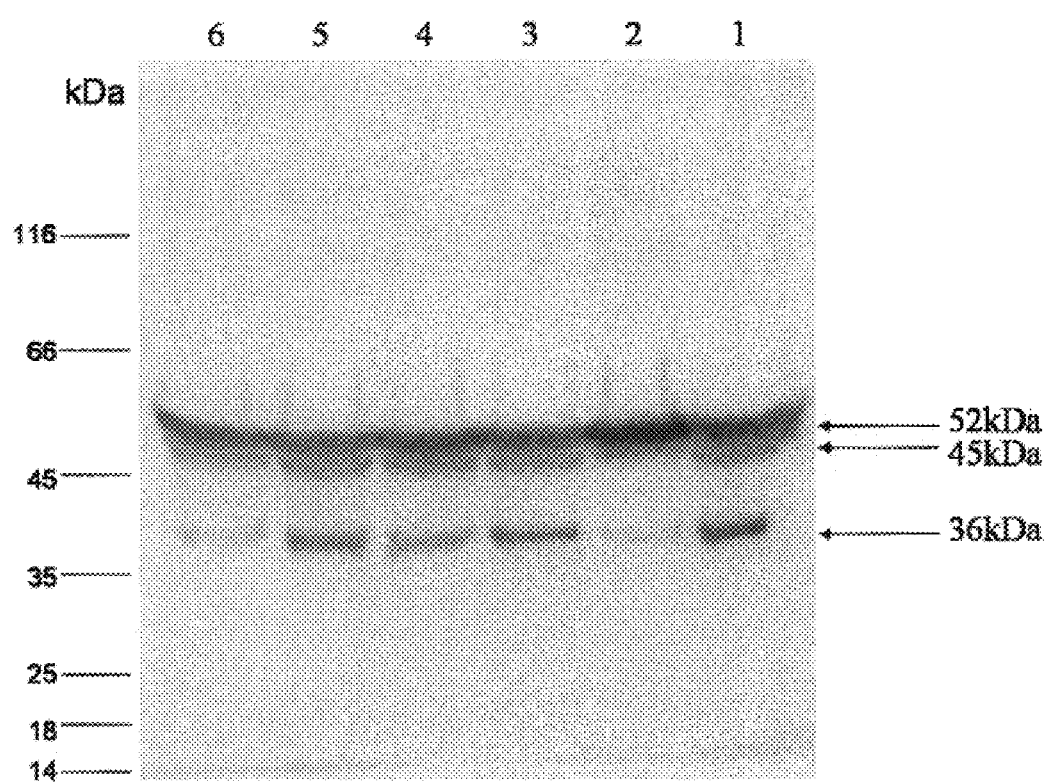
Figure 8D:
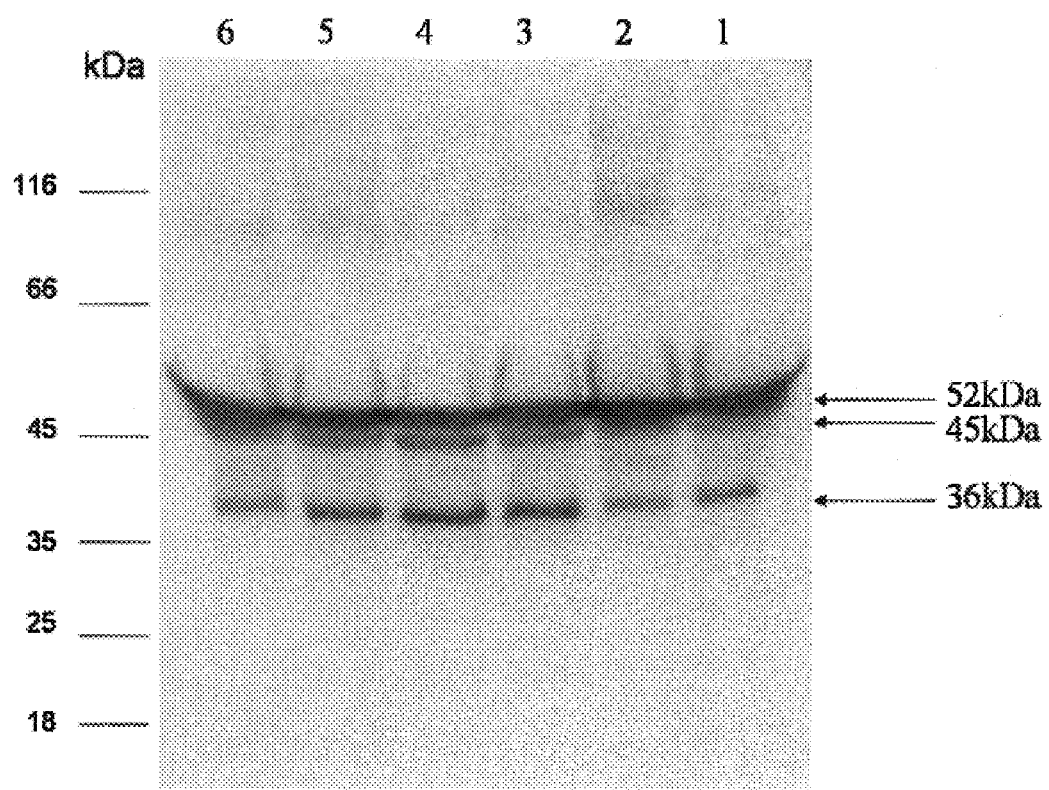
Figure 8E:
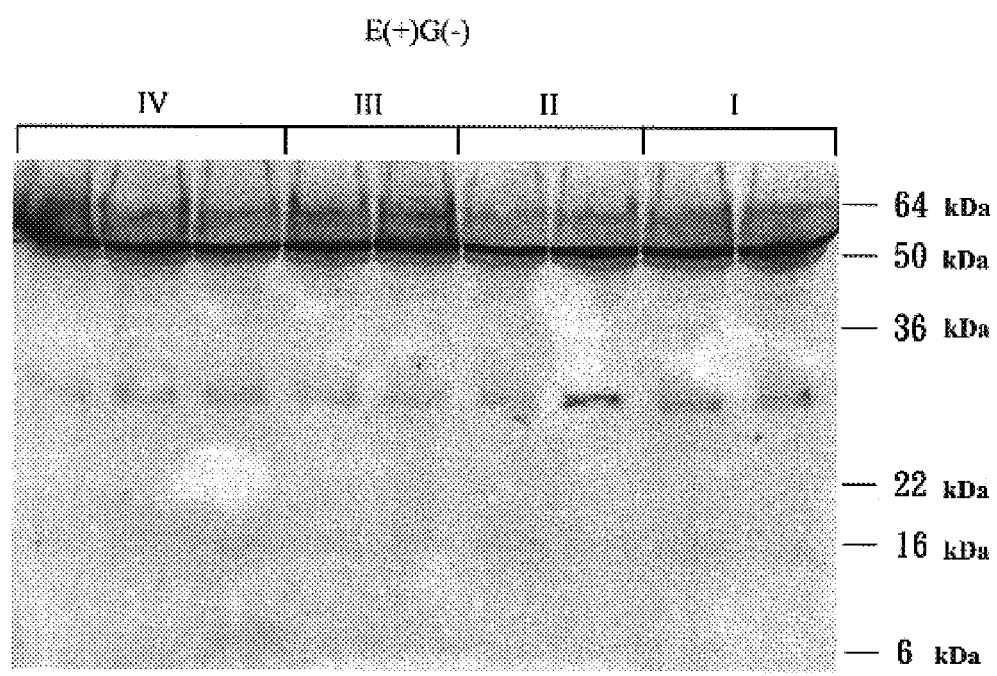
FIG. 8E shows Western blotting observations of the effect of protein loading on expressions of alpha 1-antitrypsin in peritoneal fluid specimens.

FIGS. 8A-8D show Western blotting observations of the effect of protein loading on expressions of alpha 1-antitrypsin in pooled serum specimens. The protein loadings are 10 µg/lane (A), 35 µg/lane (B), 70 µg/lane (C) and 100 µg/lane (D) where a lane represents a group: Control (Lane 1), Lane 2 (AP), Lane 3 (Adenomyosis), Lane 4 (ENDO(I/II)), Lane 5 (ENDO(□/□)), Lane 6 (ENDO+GnRHa). FIG. 8E shows the results on the peritoneal fluid samples (35 ug/lane) from patients with endometriosis at stage I, II, III, IV and without receiving the GnRHa treatment. As shown in FIGS. 8A-8E, three bands of approximate molecular weight of 52 kDa, 45 kDa, 36 kDa are detected in both serum and peritoneal samples of patients with endometriosis. In serum samples, the 36 kDa band is much more obvious in the lanes 3-5 than in other lanes. Furthermore, the 45 kDa and 36 kDa bands become visible only if the protein loading is higher than 35 µg/lane.

It can be concluded from results as follows:

1. Among all proteins showing difference in two-dimensional gel electrophoresis only alpha 1-antitrypsin exhibits significant difference in the test with immuno-dot blot. For the group with adenomyosis the concentration of alpha 1-antitrypsin in serum is not significantly higher than for the control group. It means that the change of concentration of alpha 1-antitrypsin in serum relates to an endometriosis in terms of whether endometrial cells have moved to the abdominal cavity or the pelvic cavity.

2. Two-dimensional gel electrophoresis can be used to separate proteins of different iso-electric point and different molecular weight (usually presents as in kDa) when these proteins are affected by disease due to post-translational modifications or other changes of physiological metabolism.

3. The biochemical marker of endometriosis can be the whole molecule of alpha 1-antitrypsin or fragments of alpha 1-antitrypsin with an approximate molecular weight of 52 kDa, 45 kDa or 36 kDa.

4. The concentration of alpha 1-antitrypsin in serum remains staying significantly higher than that in the healthy women at the same physiological phase during menstrual cycle in woman's body. It means that alpha 1-antitrypsin or its fragments can be taken as the biochemical marker of endometriosis in all physiological phases.

5. The concentration of alpha 1-antitrypsin can be taken as auxiliary marker used in combination with CA125 as a marker for the diagnosis of endometriosis, so as to increase the specificity of CA125 as a single marker for the diagnosis of endometriosis.

The present invention has been described above with examples of preferred embodiment thereof and it is understood that many changes and modifications in the described embodiment can be carried out without departing from the scope and the spirit of the invention as defined by the appended claims.

Based on the results described above, the present invention also provides a method of utilizing a biochemical marker comprising alpha 1-antitrypsin, fragments of alpha 1-antitrypsin, or a combination of both for endometriosis diagnosis by providing said biochemical marker with a diagnosis device. For instance, the biochemical marker can be dispersed in an organic carrier or a labeling tag, wherein the organic carrier can be organic compound or protein and the labeling tag can be fluorophor, radioisotope, or chemiluminescence. Furthermore, according to the method of utilizing a biochemical marker of the present invention, the diagnosis device may be made from polytetrafluoroethylene (such as TEFLON), plastic chip, gold sphere, magnetic bead or polymeric biomaterial such as nylon membrane, nitrocellulose, polymer or biopolymer, and the biochemical marker may be attached to the surface of the diagnosis device.

TABLE 1

| | 1-AT conc. | | Compared to each group | | | | |
|---|---|---|---|---|---|---|---|
| | n[1] | (U/ml)[2] | Control | AP | ENDO | Adenomyosis | ENDO + GnRHa |
| Control | 20 | 0.511 ± 0.116 | — | NS[3] | <0.0001 | NS | NS |
| AP | 23 | 0.764 ± 0.006 | NS | — | NS | 0.034 | NS |
| ENDO | 43 | 1.046 ± 0.006 | <0.0001 | NS | — | <0.0001 | 0.003 |
| Adenomyosis | 9 | 0.311 ± 0.006 | NS | 0.034 | <0.0001 | — | 0.01 |
| ENDO + GnRHa | 73 | 0.771 ± 0.003 | NS | NS | 0.003 | 0.01 | — |
| Total | 168 | | | | | | |

[1] n means as number.
[2] U/ml means as α1-antirypsin μg in 100 μg serum total protein
[3] NS means as non-significant.

TABLE 2

| | concentration (U/ml) | | |
|---|---|---|---|
| Patient | ENDO | ENDO + GnRHa | |
| P1 | 0.9886 | 0.4785 | ↓ |
| P2 | 0.9938 | 0.8336 | ↓ |
| P3 | 2.0909 | 1.1462 | ↓ |
| P4 | 0.9588 | 0.9222 | ↓↑ |
| P5 | 0.5201 | 0.6846 | ↑ |
| P6 | 2.9262 | 0.3931 | ↓ |
| P7 | 1.1522 | 1.3307 | ↑ |
| P8 | 1.4020 | 0.7259 | ↓ |
| P9 | 0.8275 | 0.3757 | ↓ |

TABLE 3

| | concentration (U/ml) | | | | | | |
|---|---|---|---|---|---|---|---|
| confounders | Control (n) | ENDO(I/II) (n) | p | ENDO(III/IV) (n) | p | ENDO + GnRHa (n) | p |
| Age | | | | | | | |
| 18-30(n = 23) | 0.21 ± 0.16(3) | 1.07 ± 0.32(5) | NS | —(1) | — | 0.77 ± 0.01(14) | NS |
| 31-40(n = 103) | 0.53 ± 1.50(3) | 1.03 ± 0.01(25) | 0.007 | 1.15 ± 0.21 | 0.049 | 0.90 ± 0.0(60) | NS |
| >40(n =) | —(1) | 1.01 ± 0.13(5) | — | —(0) | — | 0.93 ± 0.11(11) | — |
| BMI | | | | | | | |
| <18.5(n = 19) | — | 1.18 ± 0.23(6) | NS | 0.99 ± 0.00(2) | NS | 0.93 ± 0.14(10) | NS |
| 18.5-23(n = 102) | 0.32 ± 0.01(15) | 1.04 ± 0.01(22) | <0.0001 | 0.91 ± 0.01(3) | NS | 0.88 ± 0.01(62) | <0.0001 |
| >23(n = 15) | —(1) | 0.98 ± 0.13(6) | NS | —(0) | — | 0.91 ± 0.12(8) | NS |

TABLE 4

| ENDO | Sensitivity | 1-specificity |
|---|---|---|
| Cut-off α1-antitrysin | 74.40% | 10.00% |

TABLE 5

| Markers | Sensitivity | specificity | PPV | NPV |
|---|---|---|---|---|
| α1-antitrysin | 74.40 | 90.00 | 37.20 | 89.50 |
| CA125(35 U/ml) | 18.60 | 19.10 | 19.55 | 80.40 |
| One of them | 31.13 | 86.84 | 76.74 | 47.48 |
| Both of them | 44.44 | 78.66 | 18.60 | 92.81 |

What is claimed:

1. A method for determining whether a biochemical marker is an auxiliary marker for diagnosing endometriosis in a subject, comprising the steps of:
   (i) detecting a level of a biochemical marker selected from the group consisting of alpha 1-antitrypsin, fragments of alpha 1-antitrypsin and a combination of both, in a serum specimen from said subject, wherein said fragments have an approximate molecular weight of one of 36 kDa, 45 kDa, or 52 kDa; and
   (ii) comparing said level of said biochemical marker in the serum specimen with a baseline level of said biochemical marker, said baseline level of said biochemical marker determined through measuring levels of said biochemical marker in serum specimens from patients with endometriosis,
   wherein said subject has an age from 18 years to 40 years, and if the level of said biochemical marker in the serum specimen from the subject is greater than the baseline level of said biochemical marker, said biochemical marker is an auxiliary marker for diagnosing endometriosis.

2. The method of claim 1, wherein said biochemical marker is identified by electrophoresis in which molecules are separated according to their masses and electric charges.

3. The method of claim 1, wherein the level of said biochemical marker is measured by means of immunoassay.

4. The method of claim 1, wherein in step (ii) the baseline level of said biochemical marker is determined by analyzing a receiver operating characteristic curve with respect to a predetermined sensitivity and a predetermined specificity.

5. A method of determining whether a biochemical marker is an auxiliary marker for diagnosing endometriosis in a subject, comprising the steps of:
   (i) detecting a level of a biochemical marker selected from the group consisting of alpha 1-antitrypsin, fragments of alpha 1-antitrypsin and a combination of both, in a serum specimen from said subject, wherein said fragments have an approximate molecular weight of one of 36 kDa, 45 kDa, or 52 kDa; and
   (ii) comparing the level of said biochemical marker in the serum specimen with a baseline level of said biochemical marker, said baseline level of said biochemical marker determined through measuring levels of said biochemical marker in serum specimens from patients with endometriosis,
   wherein said subject has an age from 18 years to 40 years, and if the level of said biochemical marker in the specimen from the subject is greater than the baseline level of said biochemical marker, said biochemical marker is an auxiliary marker for diagnosing endometriosis and wherein said baseline level is 0.812 U/ml.

6. The method of claim 5, wherein said biochemical marker is identified by electrophoresis in which molecules are separated according to their masses and electric charges.

7. The method of claim 5, wherein the level of said biochemical marker is measured by means of immunoassay.

8. The method of claim 5, wherein said baseline level of said biochemical marker is determined by analyzing a receiver operating characteristic curve with respect to a predetermined sensitivity and a predetermined specificity.

* * * * *

UNITED STATES PATENT AND TRADEMARK OFFICE
CERTIFICATE OF CORRECTION

PATENT NO. : 7,399,598 B2  Page 1 of 1
APPLICATION NO. : 11/250536
DATED : July 15, 2008
INVENTOR(S) : Yang et al.

It is certified that error appears in the above-identified patent and that said Letters Patent is hereby corrected as shown below:

Column 2
Line 48, delete "scare" and insert -- scar --

Column 3
Line 16, delete "multisimensional" and insert -- multidimensional --
Line 53, delete "there" and insert -- their --

Column 4
Line 57, delete "a"

Column 7
Line 3, delete "pg" and insert -- µg --
Line 47, delete "A" from the word aAdenomyosis
Line 48, delete "endomatriosis" and insert -- endometriosis --
Line 48, delete "(ENDO)" and insert -- (ENDO(I/II)) --
Line 52, delete "endomatriosis" and insert -- endometriosis --
Line 53, delete "(ENDO)" and insert -- (ENDO(I/II)) --
Line 58, delete "EXAMPLE 4" and insert -- EXAMPLE 5 --

Column 8
Line 13, delete "pg" and insert -- µg --
Line 15, delete "EXAMPLE 4" and insert -- EXAMPLE 6 --
Line 25, delete "(ENDO(□/□))" and insert -- (ENDO(III/IV)) --
Line 26, delete "ug" and insert -- µg --

Signed and Sealed this

Twenty-third Day of September, 2008

JON W. DUDAS
*Director of the United States Patent and Trademark Office*